United States Patent
Tipler

(12) 
(10) Patent No.: US 6,494,939 B1
(45) Date of Patent: Dec. 17, 2002

(54) ZERO-DILUTION SPLIT INJECTOR LINER GAS CHROMATOGRAPHY

(75) Inventor: Andrew Tipler, Trumbull, CT (US)

(73) Assignee: PerkinElmer Instruments LLC, Shelton, CT (US)

( * ) Notice: Subject to any disclaimer, the term of this patent is extended or adjusted under 35 U.S.C. 154(b) by 27 days.

(21) Appl. No.: 09/663,314

(22) Filed: Sep. 15, 2000

Related U.S. Application Data

(60) Provisional application No. 60/154,209, filed on Sep. 16, 1999.

(51) Int. Cl.$^7$ ................................................ B01D 15/08
(52) U.S. Cl. ........................................... 96/105; 96/106
(58) Field of Search ........................... 96/101, 105, 106

(56) References Cited

U.S. PATENT DOCUMENTS

| | | | |
|---|---|---|---|
| 3,936,374 A | * | 2/1976 | Bradley et al. ............ 96/106 X |
| 4,083,702 A | * | 4/1978 | Hartigan et al. ............... 96/106 |
| 4,526,686 A | * | 7/1985 | Sisti et al. .................. 96/105 X |
| 4,559,063 A | * | 12/1985 | Munari et al. ............. 96/105 X |
| 4,787,656 A | * | 11/1988 | Ryder ........................ 96/106 X |
| 5,252,109 A | * | 10/1993 | Munari et al. ............. 96/105 X |
| 5,714,677 A | * | 2/1998 | Parsy et al. ................ 96/105 X |
| 5,889,197 A | * | 3/1999 | Van Der Maas et al. . 96/105 X |
| 6,035,697 A | * | 3/2000 | Van Der Maas et al. . 96/105 X |
| 6,042,787 A | * | 3/2000 | Pawliszyn .................. 96/105 X |
| 6,055,845 A | * | 5/2000 | Gerstel et al. ............. 96/105 X |
| 6,062,065 A | * | 5/2000 | Sugimoto et al. ......... 96/101 X |
| 6,093,371 A | * | 7/2000 | Wilson ...................... 96/105 X |

FOREIGN PATENT DOCUMENTS

| | | | | |
|---|---|---|---|---|
| DE | 2620756 A | * | 11/1977 | .................. 96/105 |
| DE | 2847308 A | * | 5/1979 | .................. 96/105 |
| DE | 2842991 A | * | 4/1980 | .................. 96/105 |
| GB | 2039777 A | * | 8/1980 | .................. 96/105 |
| JP | 63-122952 A | * | 5/1988 | .................. 96/105 |

* cited by examiner

*Primary Examiner*—Robert H. Spitzer
(74) *Attorney, Agent, or Firm*—St. Onge Steward Johnston & Reens LLC

(57) ABSTRACT

A gas chromatography split injector including a housing having a carrier gas inlet port and a vent port and an injector liner is provided. The injector liner includes a substantially cylindrical outer liner member disposed within the housing and an inner liner member disposed within the outer liner member. The inner liner member has substantially cylindrical upper and lower portions and a constriction therebetween. The constriction includes an inner surface having an inner diameter smaller than a diameter of inner surfaces of the upper and lower portions. The injector also includes a chromatographic column passing through the lower portion of the inner liner member and is in sealing engagement with the constriction of the inner liner member. A transfer line passing through the upper portion of the inner liner member and has an end located proximate to the constriction of the inner liner member. A sealing member is disposed between the outer liner member and the housing at a position between the carrier gas inlet port and the vent port.

12 Claims, 3 Drawing Sheets

ZERO-DILUTION SPLIT INJECTOR LINER GAS CHROMATOGRAPHY

CLAIM OF PRIORITY

This application claims the benefit of U.S. Provisional Patent Application No. 60/154,209, filed Sep. 16, 1999.

FIELD OF THE INVENTION

The present invention relates to a split injector liner for a vapor sampling system, such as an equilibration headspace extraction system, and more particularly to such a split injector liner which can be used to interface a vapor sampling system, via a conventional gas chromatographic split injector, to a capillary column so that there is no dilution or dispersion of the sample vapor and so that optimum chromatographic separation and detection limits are preserved.

BACKGROUND OF THE INVENTION

Certain sample extraction systems produce a homogenous sample vapor from constituent volatile organic compounds (VOCs) that can be analyzed by gas chromatography (GC). One such system is a headspace sampler whereby a liquid or solid sample is sealed in a suitable vial and placed inside a thermostatted environment. The VOCs within the sample become distributed between the sample matrix and the gaseous headspace above it and, in time, the concentration of sample vapor within the headspace reaches equilibrium. The vial is then pressurized with an inert carrier gas and a plug of the headspace vapor is allowed to elute from the vial and be introduced into a gas chromatograph where the composition of the headspace vapor is determined. The concentration of each compound within the original sample matrix is calculated by applying appropriate calibration response factors.

Many applications using such techniques require the chromatographic separation of many extracted compounds and their detection at very low levels. It is, therefore, critical to achieve an efficient transfer of the plug of the sample headspace vapor from the vial to the chromatographic column without dilution or dispersion. Any such effect would degrade component detection limits and chromatographic separation respectively.

One of two approaches is normally adopted for the interface between the vial and the chromatographic column: splitless transfer or split transfer.

In a splitless transfer interface, the chromatographic column may be effectively connected directly to the pressurized sample vial. The sample may then elute into the column without the need for additional carrier gas. This approach is termed "Pressure Balanced Sampling".

One of the problems with splitless transfer is that the flow rate from the vial to the column is very low—with narrow-bore capillary columns this may be less than 0.5 ml/min. At such low flow rates, the internal capacity of the sampling mechanism and connecting lines is significant and so a major portion of the sample plug entering the column comprises residual carrier gas from these internal voids. This in effect causes sample vapor dilution and dispersion and compromises chromatographic performance. For this reason, wider sample vapor plugs are normally selected during headspace sampling. However, although this gives better detection limits, it does reduce chromatographic separation and precludes the use of narrow-bore columns.

Moreover, some systems use a sampling valve between the vial and the column. However, this requires additional carrier gas to transfer the sample vapor from the valve to the column, and the flow rate is still low and internal voids are still present.

In a split transfer interface, a splitter may be introduced into the path between the headspace vial and the chromatographic column in order to reduce the effect of any internal voids in the sample path. This splitter allows a moderate flow rate (typically 20 ml/min) of the sample vapor to be vented from the system. This has the effect of increasing the total volumetric flow through the vial-column interface and so reduces the detrimental effects of the internal voids on the resultant chromatography.

For user convenience and flexibility, it is attractive to utilize a standard split injector, as normally used for injection of liquid samples, for the headspace splitter. However, the use of an injector in such a manner requires the use of additional carrier gas to be supplied to the injector. While this allows the control of carrier gas pressure through the column independently of the conditions applied at the sample vial, it causes significant dilution of the sample vapor before it enters the column.

Therefore, neither the splitless nor split interface approaches described above is fully able to deliver a narrow, undiluted plug of sample from the headspace vial into a narrow-bore GC capillary column.

What is desired, therefore, is a split injector liner which can be used to interface a vapor sampling system, via a conventional gas chromatographic split injector, to a capillary column so that there is no dilution or dispersion of the sample vapor and so that optimum chromatographic separation and detection limits are preserved.

SUMMARY OF THE INVENTION

Accordingly, it is an object of the present invention to provide a split injector liner which can be used with a standard GC split injector.

Another object of the present invention is to provide a split injector liner having the above characteristics and which enables the delivery of a narrow, undiluted plug of sample vapor from a pressurized headspace vial into a narrow-bore GC capillary column.

A further object of the present invention is to provide a split injector liner having the above characteristics and which improves analytical detection limits as compared to known systems.

Still another object of the present invention is to provide a split injector liner having the above characteristics and which enables faster analysis times as compared to known systems.

Yet a further object of the present invention is to provide a split injector liner having the above characteristics and which can be employed with many known GC sampling systems, such as thermal desorption, purge and trap and gas sampling valves, where sample vapor must be transferred efficiently to a GC column.

These and other objects of the present invention are achieved by provision of a gas chromatography split injector including a housing having a carrier gas inlet port and a vent port and an injector liner. The injector liner includes a substantially cylindrical outer liner member disposed within the housing and an inner liner member disposed within the outer liner member. The inner liner member has substantially cylindrical upper and lower portions and a constriction therebetween. The constriction includes an inner surface having an inner diameter smaller than a diameter of inner surfaces of the upper and lower portions. The injector also includes a chromatographic column passing through the lower portion of the inner liner member and is in sealing engagement with the constriction of the inner liner member. A transfer line passing through the upper portion of the inner liner member and has an end located proximate to the constriction of the inner liner member. A sealing member is disposed between the outer liner member and the housing at a position between the carrier gas inlet port and the vent port.

A first fluid passageway is defined by an inner surface of the inner liner member such, that the transfer line is in fluid communication with the chromatographic column therethrough. A second fluid passageway is defined by an outer surface of the transfer line and an inner surface of the inner liner member, an outer surface of the inner liner member and an inner surface of the outer liner member, and an outer surface of the outer liner member and an inner surface of the housing such that the transfer line is in fluid communication with the vent port therethrough. A third fluid passageway is defined by an outer surface of the inner liner member and an inner surface of the outer liner member, and an outer surface of the outer liner member and an inner surface of the housing such that the carrier gas inlet port is in fluid communication with the vent port therethrough.

Preferably, the split injector also includes a first pressurized gas supply supplying pressurized gas to the transfer line and a second pressurized gas supply supplying pressurized gas to the carrier gas inlet port. Most preferably, the first pressurized gas supply supplies gas at a higher pressure than the second pressurized gas supply. Also, most preferably, the end of the transfer line is positioned about 2 millimeters away from the constriction of the inner liner member.

The inner liner member preferably includes an outwardly flaring flange portion extending from an upper edge of the upper portion to facilitate insertion of the transfer line therethrough, the flange portion having an outer diameter greater than a diameter of the inner surface of the outer liner member. It is also preferable for the outer liner member to include a reduced diameter channel portion at a lower end thereof, the reduced diameter channel portion having an inner diameter smaller than an outer diameter of the lower portion of the inner liner member. Most preferably, a lower edge of the lower portion of the inner liner member is beveled such as to inhibit relative sealing between the inner liner member and the outer liner member, and a lower edge of the reduced diameter channel portion of the outer liner member includes an inwardly flaring frustoconical portion to facilitate insertion of the chromatographic column therethrough.

In another aspect, the invention comprises an injector liner which can be used with a standard gas chromatography split injector so as to create a split injector as described above.

The invention and its particular features and advantages will become more apparent from the following detailed description considered with reference to the accompanying drawings.

DETAILED DESCRIPTION OF THE INVENTION

Figure 1:
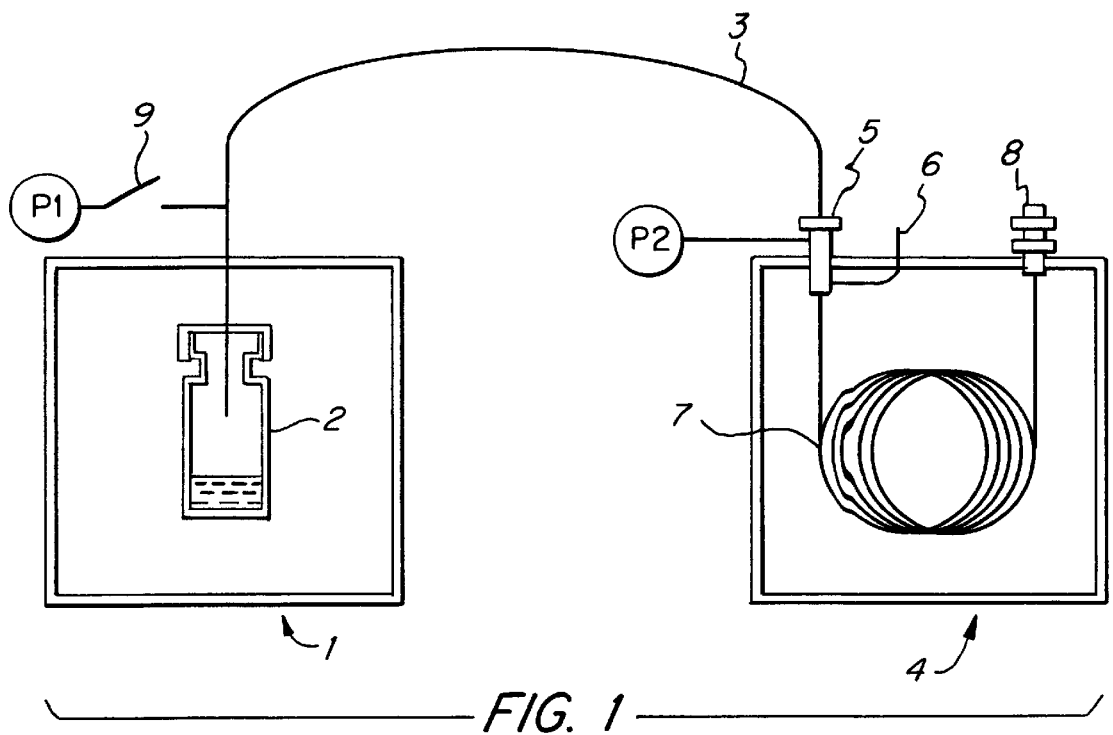
FIG. 1 is a schematic view illustrating a headspace sampler interconnected with a GC, which can employ a split injector liner in accordance with the present invention.

Referring first to FIG. 1, an overall sampling system comprises a headspace sampler 1 containing a sample vial 2, a heated tubular fused silica transfer line 3, a gas chromatograph 4, a standard liquid split injector 5 with split vent 6, a capillary gas chromatographic column 7 and a suitable detector 8. Two pressure-controlled carrier gas supplies P1 and P2 deliver carrier gas to the sample vial 2 and the chromatographic injector 5 respectively. The supply of carrier gas P1 to the sample vial 2 is switched by a solenoid valve 9.

Figure 2:
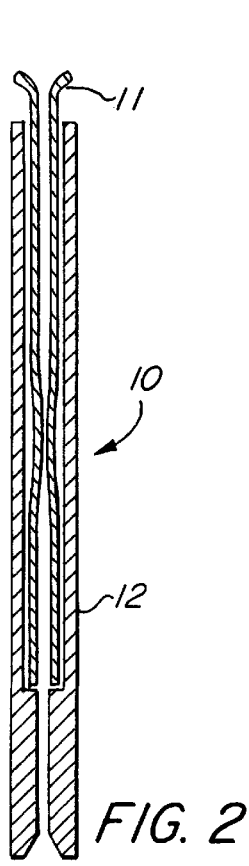
FIG. 2 is a partially cross-sectional side view illustrating a split injector liner in accordance with the present invention.
Figure 3:
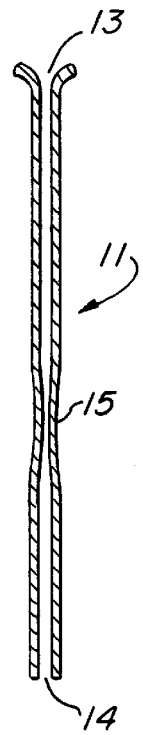
FIG. 3 is a partially cross-sectional side view illustrating an inner liner portion of the split injector liner of FIG. 2.
Figure 4:
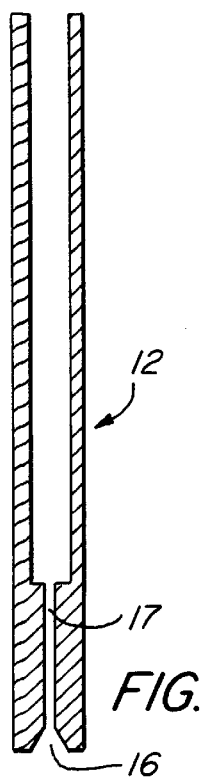
FIG. 4 is a partially cross-sectional side view illustrating an outer liner portion of the split injector liner of FIG. 2.

Referring now to FIGS. 2–4, a split injector liner 10 in accordance with the present invention is installed inside the injector 5. The liner 10 comprises two components: an inner "hourglass"-shaped insert 11 and an outer liner 12. There is a sufficient gap between the outer wall of the insert 11 and the inner wall of the outer liner 12 to allow the free passage of gas between the two, as discussed more fully below. The insert 11 is flared at the top 13 to help with the insertion of the fused silica transfer line 3 from the headspace sampler 1. The bottom of the insert 11 is beveled 14 to ensure that the insert 11 does not seal against the outer liner 12 thus ensuring free passage of gas between the two. There is an "hourglass" constriction 15 within the insert 11.

The outer liner 12 is flared at the bottom 16 to help with the insertion of the chromatographic column 7. The lower section 17 of the outer liner 12 comprises a reduced diameter channel that is aligned with the insert 11 when installed. This facilitates the insertion of the column 7 right up to the hourglass constriction 15 in the assembled liner 10.

Figure 5:
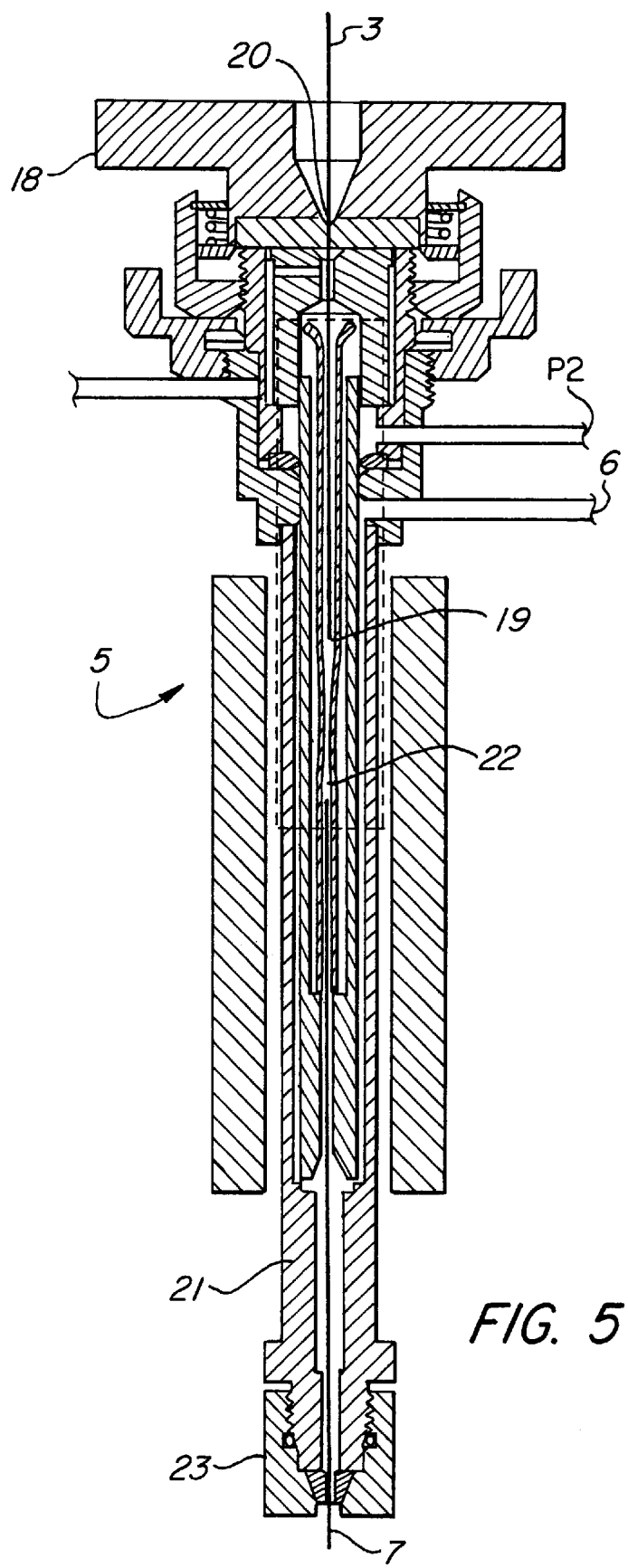
FIG. 5 is a partially cross-sectional side view illustrating the split injector liner of FIG. 2 installed inside a GC standard split injector.

Referring now to FIG. 5, the assembled liner 10 is installed inside the injector 5 in the same manner as a normal injector liner. The fused silica transfer line 3 is introduced through the top 18 of the injector 5 to a point 19 about 5 mm above the "hourglass" constriction 15 within the insert 11 and is secured at that position 19 by a suitable sealing mechanism 20. The chromatographic column 7 is introduced through the bottom of the injector 21 and is pushed up through the outer liner 12 and insert 11 until its end 22 rests against the constriction 15. The column 7 is further inserted and lifts the insert 11 up until the constriction 15 stops as it contacts the end of the transfer line 19. The column 7 is then withdrawn about 2 mm to leave that distance between the end of the transfer line 19. The insert 11 is held and is loosely sealed on the end of the column 22 by gravity. The end of the column 12 is then secured and sealed at that position by a nut and ferrule 23.

Figure 6:
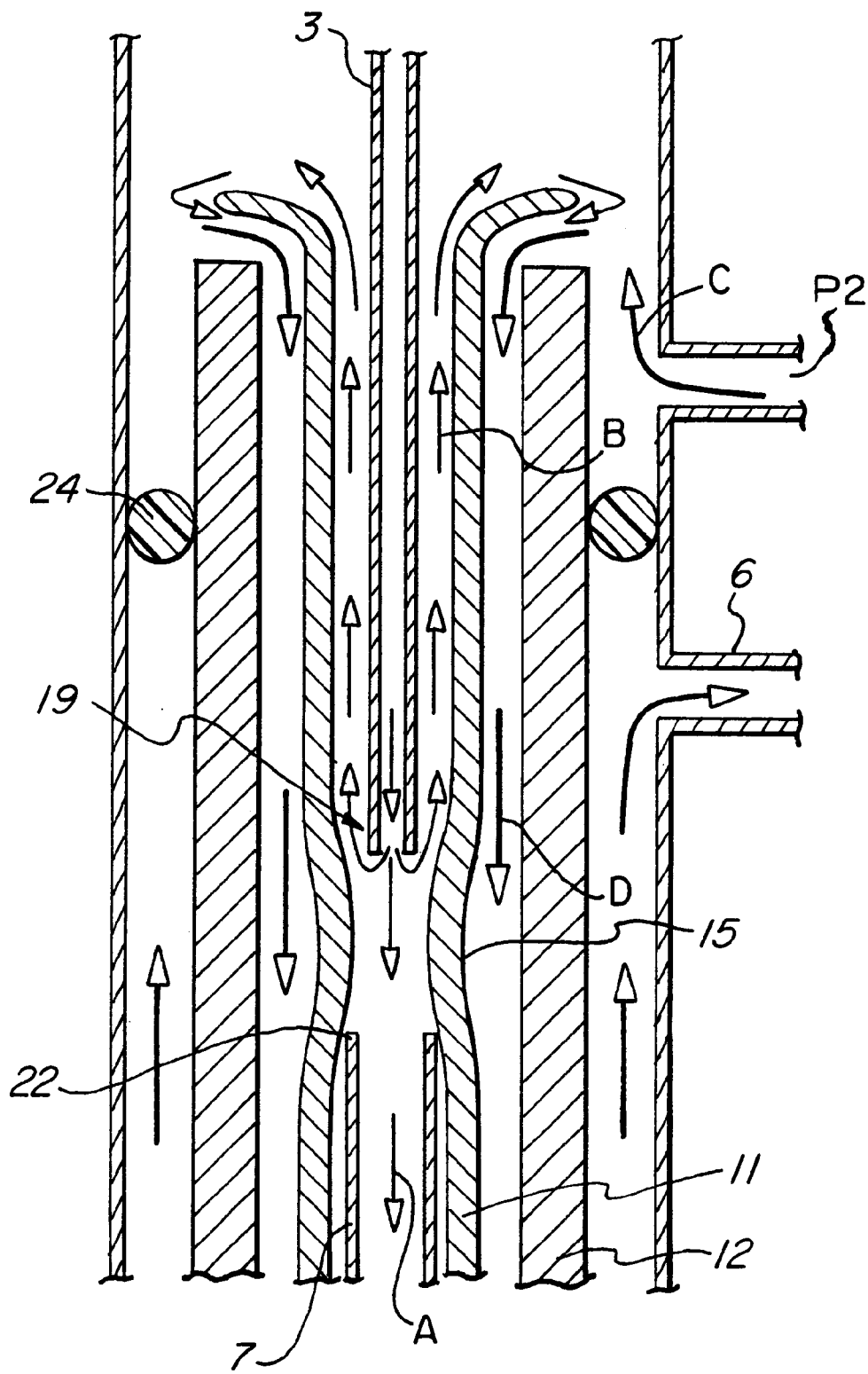
FIG. 6 is a partially cross-sectional side view illustrating the flow path of gases within and around the split injector liner of FIG. 2.

Referring now to FIG. 6, during sampling, the sample vapor inside the vial 2 is first pressurized to a pressure P1 with carrier gas by activating the solenoid valve 9. This pressure P1 must be above that in the GC injector (i.e., P2). Carrier gas is supplied to the injector 5, via the normal carrier gas supply P2, to the required pressure for the GC column 7. Carrier gas is allowed to vent through the injector splitter 6 at a rate of about 15 ml/min or more. Because the sample vapor is at a higher pressure than the injector pressure, the sample vapor will elute down the transfer line 3 and into the injector 5.

During sampling, the sample vapor will elute from the transfer line 3, into the insert 11 and immediately enter the chromatographic column 7 (indicated by arrows A). The excess vapor eluting from the transfer line 3 will exit out (indicated by arrows B) through the gap between the end of the transfer line 19 and the constriction 15 in the insert 11 and will mix with carrier gas (indicated by arrows C) flowing through the injector outer-liner 12 and out (indicated by arrows D) through the split vent 6. The carrier gas and the excess vapor are prevented from exiting directly through injector splitter 6 by a gasket 24 or the like. The excess vapor flowing out (indicated by arrows B) of the insert 11 acts as a barrier to the carrier gas flowing through the outer-liner 12 and prevents it from reaching the inlet 22 to the chromatographic column 7 and so no dilution or dispersion of the sample vapor plug is possible.

The present invention, therefore, provides a split injector liner which can be used with a standard GC split injector, which enables the delivery of a narrow, undiluted plug of sample vapor from a pressurized headspace vial into a narrow-bore GC capillary column, which improves analytical detection limits as compared to known systems, which enables faster analysis times as compared to known systems, and which can be employed with many known GC sampling systems, such as thermal desorption, purge and trap and gas sampling valves, where sample vapor must be transferred efficiently to a GC column.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An injector liner for use with a gas chromatography split injector, said injector liner comprising:
    a substantially cylindrical outer liner member;
    an inner liner member disposed within the outer liner member, said inner liner member having substantially cylindrical upper and lower portions and a constriction therebetween, the constriction having an inner surface having an inner diameter smaller than a diameter of inner surfaces of the upper and lower portions, the constriction being adapted to receive in sealing engagement therewith a chromatographic column passing through the lower portion and being adapted to receive a transfer line passing through the upper portion such that the transfer line is in fluid communication with the chromatographic column and with a space defined by an outer surface of the inner liner member and an inner surface of the outer liner member; and
    wherein said inner liner member further comprises an outwardly flaring flange portion extending from an upper edge of the upper portion to facilitate insertion of the transfer line therethrough, the flange portion having an outer diameter greater than a diameter of the inner surface of the outer liner member, and being spaced from the outer liner member such that the transfer line is in fluid communication with the space defined by an outer surface of the inner liner member and an inner surface of the outer liner member.

2. The injector liner of claim 1 wherein said outer liner member further comprises a reduced diameter channel portion at a lower end thereof, the reduced diameter channel portion having an inner diameter smaller than an outer diameter of the lower portion of said inner liner member.

3. The injector liner of claim 2 wherein a lower edge of the lower portion of said inner liner member is beveled such as to inhibit relative sealing between said inner liner member and said outer liner member.

4. The injector liner of claim 2 wherein a lower edge of the reduced diameter channel portion of said outer liner member includes an inwardly flaring frustoconical portion to facilitate insertion of the chromatographic column therethrough.

5. A gas chromatography split injector comprising:
    a housing having a carrier gas inlet port and a vent port;
    an injector liner comprising:
        a substantially cylindrical outer liner member disposed within said housing;
        an inner liner member disposed within the outer liner member, said inner liner member having substantially cylindrical upper and lower portions and a constriction therebetween, the constriction having an inner surface having an inner diameter smaller than a diameter of inner surfaces of the upper and lower portions;
        a chromatographic column passing through the lower portion of said inner liner member and being in sealing engagement with the constriction of said inner liner member;
        a transfer line passing through the upper portion of said inner liner member and having an end located proximate to the constriction of said inner liner member;
        a sealing member disposed between said outer liner member and said housing at a position between the carrier gas inlet port and the vent port;
        a first fluid passageway defined by an inner surface of said inner liner member such that said transfer line is in fluid communication with said chromatographic column therethrough;
        a second fluid passageway defined by an outer surface of said transfer line and an inner surface of said inner liner member, an outer surface of said inner liner member and an inner surface of said outer liner member, and an outer surface of said outer liner member and an inner surface of said housing such that said transfer line is in fluid communication with the vent port therethrough; and
        a third fluid passageway defined by an outer surface of said inner liner member and an inner surface of said outer liner member, and an outer surface of said outer liner member and an inner surface of said housing such that the carrier gas inlet port is in fluid communication with the vent port therethrough.

6. The split injector of claim 5 further comprising a first pressurized gas supply supplying pressurized gas to said transfer line and a second pressurized gas supply supplying pressurized gas to the carrier gas inlet port.

7. The split injector of claim 6 wherein the first pressurized gas supply supplies gas at a higher pressure than the second pressurized gas supply.

8. The split injector of claim 5 wherein the end of said transfer line is positioned about 2 millimeters away from the constriction of said inner liner member.

9. The split injector of claim 5 wherein said inner liner member further comprises an outwardly flaring flange portion extending from an upper edge of the upper portion to facilitate insertion of the transfer line therethrough, the flange portion having an outer diameter greater than a diameter of the inner surface of the outer liner member.

10. The injector liner of claim 5 wherein said outer liner member further comprises a reduced diameter channel portion at a lower end thereof, the reduced diameter channel portion having an inner diameter smaller than an outer diameter of the lower portion of said inner liner member.

11. The injector liner of claim 10 wherein a lower edge of the lower portion of said inner liner member is beveled such as to inhibit relative sealing between said inner liner member and said outer liner member.

12. The injector liner of claim 10 wherein a lower edge of the reduced diameter channel portion of said outer liner member includes an inwardly flaring frustoconical portion to facilitate insertion of the chromatographic column therethrough.

* * * * *

UNITED STATES PATENT AND TRADEMARK OFFICE
CERTIFICATE OF CORRECTION

PATENT NO.     : 6,494,939 B1                                      Page 1 of 1
DATED          : December 17, 2002
INVENTOR(S)    : Andrew Tipler It is certified that error appears in the above-identified patent and that said Letters Patent is hereby corrected as shown below:

<u>Title page,</u>
Item [54], should read:

-- [54]  ZERO-DILUTION SPLIT INJECTOR LINER FOR GAS
         CHROMATOGRAPHY --

Signed and Sealed this

First Day of April, 2003

JAMES E. ROGAN
*Director of the United States Patent and Trademark Office*